(12) United States Patent
Byun et al.

(10) Patent No.: US 11,168,094 B2
(45) Date of Patent: *Nov. 9, 2021

(54) QUINOLINONE DERIVATIVE AND PHARMACEUTICAL COMPOSITION FOR PREVENTING OR TREATING ALLERGIC DISEASES SUCH AS ASTHMA OR ATOPIC DERMATITIS INCLUDING THE QUINOLINONE DERIVATIVE AS ACTIVE INGREDIENT

(71) Applicant: Azcuris Co., Ltd., Sejong-si (KR)

(72) Inventors: Youngjoo Byun, Daejeon (KR); Young Ho Jeon, Sejong (KR); Kiho Lee, Seoul (KR); Ki Yong Lee, Sejong (KR); Yong Woo Jung, Daejeon (KR); Sang-Hyun Son, Daejeon (KR)

(73) Assignee: Azcuris Co., Ltd., Sejong-si (KR)

( * ) Notice: Subject to any disclaimer, the term of this patent is extended or adjusted under 35 U.S.C. 154(b) by 66 days.

This patent is subject to a terminal disclaimer.

(21) Appl. No.: 16/473,362

(22) PCT Filed: Jan. 4, 2018

(86) PCT No.: PCT/KR2018/000165
§ 371 (c)(1),
(2) Date: Jun. 25, 2019

(87) PCT Pub. No.: WO2018/128407
PCT Pub. Date: Jul. 12, 2018

(65) Prior Publication Data
US 2020/0140457 A1 May 7, 2020

(30) Foreign Application Priority Data

Jan. 6, 2017 (KR) .................. 10-2017-0002326
Jan. 4, 2018 (KR) .................. 10-2018-0001019

(51) Int. Cl.
*C07D 498/04* (2006.01)
*A61P 11/06* (2006.01)
*A61P 17/00* (2006.01)

(52) U.S. Cl.
CPC ............ *C07D 498/04* (2013.01); *A61P 11/06* (2018.01); *A61P 17/00* (2018.01)

(58) Field of Classification Search
CPC .................................................. C07D 498/04
See application file for complete search history.

(56) References Cited

U.S. PATENT DOCUMENTS 4,522,947 A 6/1985 Musser et al.

FOREIGN PATENT DOCUMENTS

| CN | 101270087 A | 9/2008 |
|---|---|---|
| CN | 101429200 A | 5/2009 |
| CN | 102046639 A | 5/2011 |
| CN | 102666548 A | 9/2012 |
| JP | 5-310744 A | 11/1993 |
| JP | 2010-143829 A | 7/2010 |
| KR | 10-2016-0111846 A | 9/2016 |
| WO | WO 98/08846 A1 | 3/1998 |
| WO | WO 00/09506 A1 | 2/2000 |
| WO | WO 2010/011537 A1 | 1/2010 |

OTHER PUBLICATIONS

Extended European Search Report dated May 12, 2020 Patent Application No. 18736592.9 (7 pages in English).
Shiro, Tomoya et al., "7-Phenyl-imidazoquinolin-4(5H)-one derivatives as selective and orally available mPGES-1 inhibitors", *Bioorganic & Medicinal Chemistry*, vol. 21, Issue 11, Jun. 1, 2013 (pp. 2868-2878).
Noha, Stefan M. et al., "Discovery of novel, non-acidic mPGES-1 inhibitors by virtual screening with a multistep protocol", *Bioorganic & Medicinal Chemistry*, vol. 23, Issue 15, Aug. 1, 2015 (pp. 4839-4845).
Kim, Young Kwan et al., "Discovery of an Interleukin 33 Inhibitor by Molecular Docking Simulation and NMR Analysis", *Bulletin of the Korean Chemical Society*, vol. 37, 2016 (pp. 117-118).
International Search Report dated Apr. 16, 2018 in counterpart International Patent Application No. PCT/KR2018/000165 (2 pages in English and 2 pages in Korean).
Vrijdag, Johannes L. et al. "Scaffold Hopping via a Transannular Rearrangement-Encompassing Cascade," *Organic letters*, vol. 15, No. 5, 2013 (pp. 1052-1055).
Kamijo, Seiji et al. "IL-33-Mediated Innate Response and Adaptive Immune Cells Contribute to Maximum Responses of Protease Allergen-Induced Allergic Airway Inflammation," *The Journal of Immunology*, vol. 190, No. 9, 2013 (pp. 4489-4499).
Julia, Valerie et al. "The impact of diet on asthma and allergic diseases." *Nature Reviews Immunology*, vol. 15, No. 5, May 2015 (pp. 308-322).

(Continued)

*Primary Examiner* — Emily A Bernhardt
(74) *Attorney, Agent, or Firm* — NSIP Law (57) ABSTRACT

The present invention relates to a novel quinolinone derivative compound that regulates intracellular signal transduction mediated by TSLP and IL-33 to exhibit efficacy in preventing or treating allergic diseases such as asthma or atopic dermatitis. The quinolinone derivative compound of the present invention can effectively suppress inflammatory responses of allergic diseases such as asthma or atopic dermatitis. The present invention also relates to a pharmaceutical composition including the quinolinone derivative compound. The pharmaceutical composition of the present invention can be used to fundamentally prevent or treat various allergic and asthmatic diseases.

3 Claims, 5 Drawing Sheets

(56) References Cited

OTHER PUBLICATIONS

Merchant, J. R., et al., "A Simple Method for the Synthesis of 5-Methyloxazolo [4, 5-c] quinolin-4 (5 H)-ones," *Bulletin of the Chemical Society of Japan*, vol. 50, No. 11, 1977 (pp. 3075-3075).
Chinese Office Action dated May 8, 2021 in counterpart Chinese Patent Application No. 201880005933.6 (10 pages in English and 7 pages in Chinese).

QUINOLINONE DERIVATIVE AND PHARMACEUTICAL COMPOSITION FOR PREVENTING OR TREATING ALLERGIC DISEASES SUCH AS ASTHMA OR ATOPIC DERMATITIS INCLUDING THE QUINOLINONE DERIVATIVE AS ACTIVE INGREDIENT

CROSS REFERENCE TO RELATED APPLICATIONS

This application is a U.S. National Stage Application of International Application No. PCT/KR2018/000165, filed on Jan. 4, 2018, which claims the benefit under 35 USC 119(a) and 365(b) of Korean Patent Application No. 10-2017-0002326, filed on Jan. 6, 2017 and Korean Patent Application No. 10-2018-0001019, filed on Jan. 4, 2018, in the Korean Intellectual Property Office, the entire disclosure of which is incorporated herein by reference for all purposes.

TECHNICAL FIELD

The present invention relates to a novel quinolinone derivative, and more specifically to a 4- or 5-substituted 2-aryl-oxazolo[4,5-c]quinolin-4(5H)-one as a quinolinone derivative compound that regulates signal transduction mediated by TSLP and IL-33 to exhibit efficacy in preventing or treating allergic diseases such as asthma or atopic dermatitis, and a pharmaceutical composition for preventing or treating allergic diseases such as asthma or atopic dermatitis including the quinolinone derivative compound as an active ingredient.

BACKGROUND ART

Treatment of allergic inflammatory diseases with bronchodilators and anti-inflammatory agents is based on allopathy. These therapeutic agents are temporarily effective in ameliorating symptoms of allergic diseases but cannot basically control allergic diseases, failing to fundamentally treat the diseases.

Environmental diseases such as bronchial asthma, atopic skin diseases, and allergic rhinitis are known as immune diseases and Th2 cells are well known to play a pivotal role in causing allergic responses. When stimulated by an antigen in lymphocytes, CD4 T cells can differentiate into various types of Th cells depending on cytokines recognized simultaneously by the cells. When the recognized cytokines are type 2 cytokines, such as thymic stromal lymphopoietin (TSLP) or IL-4, such cells differentiate into Th2 to cause allergic responses.

Interleukin-33 (IL-33) is an innate cytokine produced mainly by mucosal epithelial cells when various external stimuli are applied. IL-33 is known to play an important role in regulating allergic immune responses, mainly asthma, mediated by Th2 cells. The IL-33 receptor complex for IL-33-mediated signaling consists of IL-33 as a ligand, ST2 (IL-1R4) as a ligand binder, and IL-1 receptor accessory protein (IL-IRAcP) as a signal transducer. Th2 inflammatory cytokines, including IL-4, IL-5, IL-6, IL-13 and IL-8, and chemokines are produced by stimulation of IL-33. When bound with IL-33, the IL-33 receptor complex activates molecules of downstream signaling systems such as NF-kB and AP-1 through IL-1 receptor-associated kinase (IRAK), TNF receptor associated factor 6 (TRAF6), and/or MAPKs. Overall, it is expected that allergic diseases can be basically treated by the regulation of TSLP and IL-33, cytokines that play important roles in the differentiation of Th2 cells.

PRIOR ART DOCUMENTS

Non-Patent Document 1: Julia V, Macia L, Dombrowicz D. Nat Rev Immunol. 2015; 15:308-322.

Non-Patent Document 2: S. Kamijo, H. Takeda, T. Tokura, M. Suzuki, K. Inui, M. Hara, H. Matsuda, A. Matsuda, K. Oboki, T. Ohno, H. Saito, S. Nakae, K. Sudo, H. Suto, S. Ichikawa, H. Ogawa, K. Okumura, T. Takai, IL-33-mediated innate response and adaptive immune cells contribute to maximum responses of protease allergen-induced allergic airway inflammation, J Immunol, 190 (2013) 4489-4499.

DETAILED DESCRIPTION OF THE INVENTION

Problems to be Solved by the Invention

Thus, the present invention intends to provide a novel quinolinone derivative that regulates intracellular signal transduction mediated by TSLP and IL-33 to exhibit efficacy in preventing or treating allergic diseases such as asthma or atopic dermatitis.

The present invention also intends to provide a pharmaceutical composition for preventing or treating allergic diseases such as asthma or atopic dermatitis including the novel quinolinone derivative as an active ingredient and a pharmaceutically acceptable carrier.

Means for Solving the Problems

One aspect of the present invention provides a quinolinone derivative represented by Formula 1a or 1b:

[Formula 1a]

[Formula 1b]

A description will be given concerning the structures and substituents of Formulae 1a and 1b and specific examples of the quinolinone derivatives.

The present invention also provides a pharmaceutical composition for preventing or treating allergic diseases such as asthma or atopic dermatitis including the novel derivative represented by Formula 1a or 1b as an active ingredient and a pharmaceutically acceptable carrier.

Effects of the Invention

The quinolinone derivative compound of the present invention can effectively suppress inflammatory responses of allergic diseases such as asthma or atopic dermatitis.

In addition, the pharmaceutical composition of the present invention can be used to fundamentally prevent or treat various allergic diseases such as asthma or atopic dermatitis.

BEST MODE FOR CARRYING OUT THE INVENTION

The present invention will now be described in more detail.

The inventors of the present invention have found that quinolinone derivatives represented by Formulae 1a and 1b effectively inhibit TSLP and IL-33, key cytokines inducing allergic diseases such as asthma or atopic dermatitis, from binding to their receptors. The present invention has been accomplished based on this finding.

One aspect of the present invention is directed to a quinolinone derivative represented by Formula 1a or 1b:

[Formula 1a]

wherein $R_1$ and $R_2$ may be identical to or different from each other and are each independently selected from $C_1$-$C_4$ alkyl groups, $C_1$-$C_4$ alkylene groups, and —Z-alkyl (wherein Z is a heteroatom selected from O, S, and N or is —$(CH_2)_m$— wherein m is an integer from 0 to 5), X and Y are each independently selected from hydrogen (H), halogen groups (fluoro (F), chloro (Cl), bromo (Br), and iodo (I)), a hydroxyl group (OH), an amino group ($NH_2$), a nitro group ($NO_2$), a cyano group (CN), a trifluoromethyl group ($CF_3$), CO—R' (wherein R' is a $C_1$-$C_4$ alkyl group), NHR' (wherein R' is a $C_1$-$C_4$ alkyl group), NR'R' (wherein each R' is independently a $C_1$-$C_4$ alkyl group), NHCOR' (wherein R' is a $C_1$-$C_4$ alkyl group), and COOR' (wherein R' is a $C_1$-$C_4$ alkyl group), p is an integer from 0 to 4, provided that when p is an integer of 2 or more, the Y groups may be identical to or different from each other, and q is an integer from 0 to 5, provided that when q is an integer of 2 or more, the X groups may be identical to or different from each other,

[Formula 1b]

wherein $R_1$, $R_2$, X, Y, p, and q are as defined in Formula 1a.

The quinolinone derivative represented by Formula 1a or 1b regulates intracellular signal transduction mediated by TSLP and IL-33 and inhibits the binding of thymic stromal lymphopoietin (TSLP) to TSLP receptor or the binding of IL-33 to ST-2.

Specifically, the quinolinone derivative represented by Formula 1a or 1b may be selected from, but not limited to, the compounds of Formulae 2 to 15:

[Formula 2]

[Formula 3]

[Formula 4]

[Formula 5]

[Formula 6]

[Formula 7]

[Formula 8]

[Formula 9]

[Formula 10]

[Formula 11]

[Formula 12]

[Formula 13]

[Formula 14]

[Formula 15]

The quinolinone derivative of the present invention can be prepared through a series of successive reactions: Sandmeyer reaction, Suzuki-coupling reaction in the presence of a palladium catalyst, Heck reaction, nitro reduction, cyclization under basic conditions, and substitution. For example, the quinolinone derivative represented by Formula 1a or 1b may be prepared by the following procedure. First, ethyl 2-chlorooxazole-4-carboxylate is obtained by Sandmeyer reaction of ethyl 2-aminooxazole-4-carboxylate as a starting material. Then, the ethyl 2-chlorooxazole-4-carboxylate is allowed to react with a substituted arylboronic acid to synthesize a 2-aryloxazole-4-carboxylate derivative. Subsequently, the 2-aryloxazole-4-carboxylate derivative is subjected to Heck reaction with 2-iodo-1-nitrobenzene to prepare a substituted 2-aryl-5-aryloxazole-4-carboxylate derivative. The nitro group of the substituted 2-aryl-5-aryloxazole-4-carboxylate derivative is reduced by hydrogenation. An intramolecular reaction between the ester group and the amine group under basic conditions and a subsequent substitution reaction with dialkylethyl bromide under basic conditions give the quinolinone derivative represented by Formula 1a or 1b.

More specifically, the compounds of Formulae 2 to 13 can be synthesized by the following reaction schemes:

°Reagents and Conditions: (i) t-BuONO, CuCl$_2$, acetonitrile, 80° C., 2 h, (64%); (ii) p-RPhB(OH)$_2$, Pd(PPh$_3$)$_4$, PhMe, H$_2$O, K$_2$CO$_3$, 90° C., 1 h;
(iii) 2-IC$_6$H$_4$NO$_2$, Pd(OAc)$_2$, PPh$_3$, Cs$_2$CO$_3$, DMF, 140° C., 3 h; (iv) 10% Pd/C, MeOH, H$_2$, 1 h; (v) DMF, H$_2$O, 2 M K$_2$CO$_3$, 90° C., 12 h; (vi) (CH$_3$)$_2$NCH$_2$CH$_2$BrHBr, K$_2$CO$_3$, DMF, 130° C., 3 h.

[2]

12 (KB 1520), 14%

13 (KB 1521), 8%

*Reagents and Conditions: (vii) (CH₃CH₂)₂NCH₂CH₂Br HBr, K₂CO₃, DMF, 130° C., 5 h.

[3]

25b. R = F
25d. R = CF₃

12 (KB 1520), R = F (14%)
14 (KB 1524), R = CF₃ (27%)

13 (KB 1521), R = F (8%)
15 (KB 1525), R = CF₃ (50%)

Reagents and Conditions: (vii) (CH₃CH₂)₂NCH₂CH₂BrHBr, K₂CO₃, DMF, 130° C., 5 h.

Reaction scheme [1] schematically shows a synthetic route to the quinolinone derivative of Formula 1a or 1b wherein both $R_1$ and $R_2$ are methyl groups, and Reaction schemes [2] and [3] schematically show synthetic routes to the quinolinone derivative of Formula 1a or 1b wherein both $R_1$ and $R_2$ are ethyl groups.

A further aspect of the present invention is directed to a pharmaceutical composition for preventing or treating an allergic disease such as asthma or atopic dermatitis including the quinolinone derivative represented by Formula 1a or 1b as an active ingredient. The pharmaceutical composition of the present invention regulates intracellular signal transduction mediated by TSLP and IL-33 and inhibits the binding of thymic stromal lymphopoietin (TSLP) to TSLP receptor or the binding of IL-33 to ST-2.

The pharmaceutical composition of the present invention can be used to prevent and treat a wide range of allergic diseases such as asthma or atopic dermatitis. Examples of the allergic diseases include, but not limited to, atopic dermatitis, urticarial rhinitis, allergic rhinitis, and asthmatic diseases.

The pharmaceutical composition of the present invention may be complexed with other known drugs for the prevention and treatment of allergic diseases such as asthma or atopic dermatitis before administration or may further include one or more other additives selected from carriers, diluents, adjuvants, and stabilizers.

The dosage form of the composition according to the present invention may vary depending on the mode of administration desired. Examples of such dosage forms include, but not limited to, solid, semi-solid, and liquid formulations, such as tablets, pills, powders, capsules, gels, ointments, emulsions, and suspensions. The composition of the present invention may be administered in unit dosage forms suitable for single administration of precise dosages. The composition of the present invention may be administered orally or parenterally. For parenteral administration, the composition of the present invention may be administered intravenously, subcutaneously or intramuscularly.

Depending on the formulation desired, the composition may further include one or more pharmaceutically acceptable carriers, diluents, adjuvants, and stabilizers, which are defined as aqueous-based vehicles commonly used to formulate pharmaceutical compositions for human administration.

The term "carrier" means a substance that facilitates the incorporation of a compound into cells or tissues. Examples of suitable carriers include, but not limited to, carbohydrate-based compounds, such as lactose, amylose, dextrose, sucrose, sorbitol, mannitol, starch, and cellulose, gum acacia, calcium phosphate, alginate, gelatin, calcium silicate, microcrystalline cellulose, polyvinylpyrrolidone, cellulose, water, syrups, salt solutions, alcohols, gum Arabic, vegetable oils, such as corn oil, cotton seed oil, soybean oil, olive oil, and coconut oil, polyethylene glycol, methyl cellulose, methyl hydroxybenzoate, propyl hydroxybenzoate, talc, magnesium stearate, and mineral oils, which are commonly used to formulate pharmaceutical compositions. The term "diluent" is defined as a substance diluted in water that can dissolve the compound of interest as well as stabilize the biologically active form of the compound. Examples of suitable diluents include distilled water, physiological saline, Ringer's solution, dextrose solution, and Hank's solution. The stabilizers can be selected from the group consisting of proteins, carbohydrates, buffers, and mixtures thereof. The composition of the present invention may optionally further include one or more additives. Examples of such optional additives include, but not limited to, lubricating agents, wetting agents, sweetening agents, flavoring agents, emulsifying agents, suspending agents, and preservatives.

Such additional additives as carriers, diluents, adjuvants, and stabilizers may be used in amounts effective to acquire pharmaceutically acceptable formulations in view of the solubility, biological activity, and other characteristics of the active ingredient.

As used herein, the term "prevent" or "preventing" refers to inhibiting a disease or disorder from occurring in an animal or human that may be predisposed to the disease or disorder but has not yet been diagnosed as having it. As used herein, the term "treat" or "treating" refers to inhibiting the development of a disease or disorder or ameliorating or eliminating the disease or disorder.

As used herein, the term "including as an active ingredient" means the presence of the corresponding ingredient in an amount necessary or sufficient to achieve a desired biological effect. In real applications, the active ingredient is used in a therapeutically effective amount to treat a target disease and such an amount can suitably be determined taking into consideration other toxicities caused by the active ingredient. For example, the amount of the active ingredient may vary depending on various factors, such as the disease or condition to be treated, the dosage form of the composition, the size of a subject or the severity of the disease or condition. The effective amount of the composition can be empirically determined by those skilled in the art without excessive experiments.

By "pharmaceutically acceptable" is meant that the biological activity and properties of the compound are not impaired.

Other terms and abbreviations used herein may be understood as their meanings recognized generally by those skilled in the art, unless otherwise defined.

MODE FOR CARRYING OUT THE INVENTION

The present invention will be explained in more detail with reference to the following examples. These examples are provided to assist in understanding the invention and are not intended to limit the scope of the invention.

Synthesis Examples: Synthesis of Inventive Quinolinone Derivatives

The inventive quinolinone derivatives of Formulae 2-15 were synthesized according to reaction schemes [1], [2], and [3].

(a) Ethyl 2-chlorooxazole-4-carboxylate (21) as intermediate

Ethyl 2-aminooxazole-4-carboxylate (468 mg, 3 mmol) was added to t-butylnitrite (540 µl, 0.45 mmol) and copper chloride (600 mg, 4.5 mmol) in acetonitrile (22 ml) at 60° C. The mixture was heated at 80° C. for 1 h. After cooling, the mixture was partitioned with dichloromethane, ice, and hydrochloric acid. The aqueous layer was further extracted with dichloromethane. The organic layer was washed with brine, dried over $MgSO_4$, and evaporated. The crude product was purified by silica gel column chromatography (hexane/$Et_2O$, 7:1 to 4:1, v/v) to afford Intermediate 21 (338 mg, 64%) as a fluffy white solid.

$R_f$=0.38 (hexane/$Et_2O$=2:1, v/v). $^1H$ NMR (300 MHz, $CDCl_3$) δ ppm 8.20 (s, 1H), 4.40 (q, J=7.2 Hz, 2H), 1.39 (t, J=6.9 Hz, 3H). LRMS (ESI) m/z 176.1 $[M+H]^+$.

(b) Synthesis of Ethyl 2-Aryloxazole-4-Carboxylate Derivatives as Intermediates Through Suzuki Reaction (1) Ethyl 2-chlorooxazole-4-carboxylate (257 mg, 1.47 mmol), 4-fluorophenylboronic acid (252 mg, 1.8 mmol, 1.2 eq.), and tetrakis(triphenylphosphine)palladium(0) (85 mg, 0.07 mmol, 0.05 eq.) were dissolved in toluene (20 mL) and a 2 M potassium carbonate solution (2.0 mL, 4.0 mmol) under a nitrogen atmosphere at room temperature. The solution was refluxed with stirring for 1 h. After cooling to room temperature, the reaction mixture was partitioned with ethyl acetate and a 2 M sodium hydroxide solution. The aqueous layer was washed twice with ethyl acetate. The organic layer washed with brine, dried over $MgSO_4$, and concentrated in vacuo. The crude product was purified by silica gel column chromatography (hexane/$Et_2O$, 5:1 to 3:1, v/v) to afford Intermediate 22b (250 mg, 73%) as a fluffy white solid.

$R_f$=0.30 (hexane/$Et_2O$=2:1, v/v). $^1H$ NMR (300 MHz, $CDCl_3$) δ ppm 8.25 (s, 1H), 8.11 (dd, J=5.4 and 8.9 Hz, 2H), 7.16 (t, J=9.0 Hz, 2H), 4.42 (q, J=7.2 Hz, 2H), 1.40 (t, J=7.2 Hz, 3H); $^{13}C$ NMR (75 MHz, $CDCl_3$) δ ppm 166.2, 162.9, 161.7, 161.3, 143.7, 134.7, 129.2, 129.1, 122.8, 122.8, 116.3, 116.1, 116.0, 115.7, 61.4, 14.3. LRMS (ESI) m/z 257.8 $[M+Na]^+$. HRMS (ESI) m/z calculated for $C_{12}H_{10}FNO_3Na^+$ $[M+Na]^+$: 258.0537; found: 258.0528.

(2) Ethyl 2-phenyloxazole-4-carboxylate (22a)

$R_f$=0.30 (hexane/$Et_2O$=2:1, v/v). $^1H$ NMR (300 MHz, $CDCl_3$) δ ppm 8.28 (s, 1H), 8.12 (dd, J=2.1 and 7.2 Hz, 2H), 7.16 (dd, J=1.8 and 5.3 Hz, 2H), 4.43 (q, J=7.2 Hz, 2H), 1.41 (t, J=7.2 Hz, 3H). LRMS (ESI) m/z 218.0 $[M+H]^+$ and 239.9 $[M+Na]^+$.

(3) Ethyl 2-(4-chlorophenyl)oxazole-4-carboxylate (22c)

$R_f$=0.38 (hexane/Et$_2$O=2:1, v/v). $^1$H NMR (300 MHz, CDCl$_3$) δ ppm 8.27 (s, 1H), 8.05 (d, J=8.4 Hz, 2H), 7.45 (d, J=7.2 Hz, 2H), 4.43 (q, J=7.2 Hz, 2H), 1.40 (t, J=7.2 Hz, 3H). LRMS (ESI) m/z 251.8 [M+H]$^+$ and 273.8 [M+Na]$^+$.

(4) Ethyl 2-(4-(trifluoromethyl)phenyl)oxazole-4-carboxylate (22d)

$R_f$=0.38 (hexane/Et$_2$O=2:1, v/v). $^1$H NMR (300 MHz, CDCl$_3$) δ ppm 8.32 (s, 1H), 8.24 (d, J=8.1 Hz, 2H), 7.74 (d, J=8.1 Hz, 2H), 4.45 (q, J=7.2 Hz, 2H), 1.42 (t, J=7.2 Hz, 3H). LRMS (ESI) m/z 286.0 [M+H]$^+$ and 308.1 [M+Na]$^+$.

(5) Ethyl 2-(4-methoxyphenyl)oxazole-4-carboxylate (22e)

$R_f$=0.13 (hexane/Et$_2$O=2:1, v/v). $^1$H NMR (300 MHz, CDCl$_3$) δ ppm 8.24 (s, 1H), 8.06 (d, J=9.0 Hz, 2H), 6.98 (d, J=9.0 Hz, 2H), 4.43 (q, J=7.2 Hz, 2H), 1.42 (t, J=7.2 Hz, 3H). LRMS (ESI) m/z 247.7 [M+H]$^+$ and 269.9 [M+Na]$^+$.

(c) Synthesis of ethyl 2-aryl-5-aryloxazole-4-carboxylate Derivatives as Intermediates by Heck Reaction (1) A mixture of 22b (192 mg, 0.8 mmol), 2-iodonitrobenzene (398 mg, 1.6 mmol, 2.0 eq.), palladium acetate (11.2 mg, 0.05 mmol, 0.06 eq.), triphenylphosphine (21 mg, 0.08 mmol, 0.1 eq.), cesium carbonate (651.6 mg, 2.0 mmol, 2.5 eq.), and DMF (4 mL) was flushed with nitrogen and heated at 140° C. for 3 h. After cooling, the reaction mixture was diluted with ethyl acetate, washed with water and brine, dried over MgSO$_4$, and concentrated in vacuo. The crude product was purified by silica gel column chromatography (hexane/Et$_2$O, 5:1 to 1:1, v/v) to afford Intermediate 23b (192 mg, 67%) as a yellow needle-like crystal.

$R_f$=0.35 (hexane/Et$_2$O=1:1, v/v). $^1$H NMR (300 MHz, CDCl$_3$) δ ppm 8.20 (d, J=8.1 Hz, 1H), 8.14 (q, J=8.4 Hz, 1H), 8.18-8.09 (m, 1H), 7.83-7.65 (m, 3H), 7.19 (t, J=8.7 Hz, 2H), 4.34 (q, J=7.2 Hz, 2H), 1.29 (t, J=7.2 Hz, 3H); $^{13}$C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 357.4 [M+H]$^+$, 379.0 [M+Na]$^+$, and 395.0 [M+K]$^+$. HRMS (ESI) m/z calculated for C$_{18}$H$_{14}$FN$_2$O$_5^+$ [M+H]$^+$: 357.0881; found: 357.0865.

(2) Ethyl 5-(2-nitrophenyl)-2-phenyloxazole-4-carboxylate (23a)

$R_f$=0.23 (hexane/Et$_2$O=1:1, v/v). $^1$H NMR (300 MHz, CDCl$_3$) δ ppm 8.19 (d, J=7.8 Hz, 1H), 8.16-8.08 (m, 1H), 8.12 (d, J=7.8 Hz, 1H), 7.76-7.66 (m, 1H), 7.77 (d, J=4.2 Hz, 2H), 7.55-7.43 (m, 3H), 4.32 (q, J=7.2 Hz, 2H), 1.27 (t, J=7.2 Hz, 3H). LRMS (ESI) m/z 339.3 [M+H]$^+$, 361.1 [M+Na]$^+$, and 377.0 [M+Na]$^+$. HRMS (ESI) m/z calculated for C$_{18}$H$_{14}$N$_2$O$_5$Na$^+$ [M+Na]$^+$: 361.0795; found: 361.0778.

(3) Ethyl 2-(4-chlorophenyl)-5-(2-nitrophenyl)oxazole-4-carboxylate (23c)

$R_f$=0.30 (hexane/Et$_2$O=1:1, v/v). $^1$H NMR (300 MHz, CDCl$_3$) δ ppm 8.18 (d, J=8.1 Hz, 1H), 8.05 (dd, J=4.2 and 10.1 Hz, 1H), 8.05 (d, J=8.7 Hz, 1H), 7.81-7.65 (m, 3H), 7.46 (d, J=8.7 Hz, 1H), 7.46 (dd, J=4.2 and 9.3 Hz, 1H), 4.31 (q, J=7.2 Hz, 2H), 1.26 (t, J=7.2 Hz, 3H); $^{13}$C NMR (75 MHz, CDCl$_3$) δ ppm 161.2, 160.5, 151.1, 148.5, 137.6, 132.8, 132.6, 131.3, 130.3, 129.2, 128.6, 124.9, 124.6, 122.6, 61.6, 29.7, 14.0. LRMS (ESI) m/z 373.1 [M+H]$^+$, 395.0 [M+Na]$^+$, and 411.0 [M+k]$^+$. HRMS (ESI) m/z calculated for C$_{18}$H$_{14}$ClN$_2$O$_5^+$ [M+H]$^+$: 373.0586; found: 373.0589.

(4) Ethyl 5-(2-nitrophenyl)-2-(4-(trifluoromethyl)phenyl)oxazole-4-carboxylate (23d)

$R_f$=0.20 (hexane/Et$_2$O=1:1, v/v). $^1$H NMR (300 MHz, CDCl$_3$) δ ppm 8.24 (d, J=8.1 Hz, 2H), 8.21 (d, J=10.5 Hz, 1H), 7.86-7.68 (m, 5H), 4.32 (q, J=7.2 Hz, 2H), 1.27 (t, J=7.2 Hz, 3H); $^{13}$C NMR (75 MHz, CDCl$_3$) δ ppm 166.1.1, 159.9, 151.7, 148.5, 133.0, 132.6, 127.3, 126.0, 125.9, 124.9, 61.8, 14.0. LRMS (ESI) m/z 407.0 [M+H]$^+$, 428.7 [M+Na]$^+$, and 445.3 [M+K]$^+$. HRMS (ESI) m/z calculated for C$_{18}$H$_{14}$F$_3$N$_2$O$_5^+$ [M+H]$^+$: 407.0849; found: 407.0809.

(5) Ethyl 2-(4-methoxyphenyl)-5-(2-nitrophenyl)oxazole-4-carboxylate (23e)

$R_f$=0.20 (hexane/Et$_2$O=1:1, v/v). $^1$H NMR (300 MHz, CDCl$_3$) δ ppm 8.18 (d, J=8.7 Hz, 1H), 8.07 (d, J=8.7 Hz, 2H), 7.82-7.64 (m, 3H), 7.00 (t, J=9.0 Hz, 2H), 4.33 (q, J=7.2 Hz, 2H), 1.28 (t, J=7.2 Hz, 3H); $^{13}$C NMR (75 MHz, CDCl$_3$) δ ppm 162.1, 161.5, 161.5, 150.4, 148.5, 132.8, 132.6, 131.1, 130.0, 128.8, 124.8, 122.8, 118.8, 114.3, 61.5, 55.5, 29.7, 14.1. LRMS (ESI) m/z 369.1 [M+H]$^+$, 391.1 [M+Na]$^+$, and 407.1 [M+K]$^+$. HRMS (ESI) m/z calculated for C$_{19}$H$_{17}$N$_2$O$_6^+$ [M+H]$^+$: 369.1081; found: 369.1090.

(d) Synthesis of Amine Derivatives as Intermediates Through Hydrogenation

(1) Ethyl 5-(2-aminophenyl)-2-(4-fluorophenyl)oxazole-4-carboxylate (24b)

A palladium catalyst was added to a solution of 23b (192 mg, 0.54 mmol) in MeOH (15 mL). The mixture was stirred under a hydrogen atmosphere (50 psi) for 1 h. The reaction mixture was filtered through a bed of Celite and volatiles were removed by reduction to afford Intermediate 24b (145 mg, 82%) as a yellow solid.

$R_f$=0.30 (hexane/Et$_2$O=1:1, v/v). $^1$H NMR (300 MHz, CDCl$_3$) δ ppm 8.18-8.07 (m, 1H), 8.12 (q, J=8.4 Hz, 1H), 7.43 (dd, J=1.2 and 7.8 Hz, 1H), 7.29 (td, J=8.1 and 1.5 Hz, 1H), 7.22-7.08 (m, 1H), 7.16 (t, J=8.4 Hz, 1H), 6.84 (td, J=7.8 and 1.2 Hz, 1H), 6.82 (d, J=8.1 Hz, 1H), 4.39 (q, J=7.2 Hz, 2H), 4.16 (bs, 2H), 1.34 (t, J=7.2 Hz, 3H); $^{13}$C NMR (75 MHz, CDCl$_3$) δ ppm 166.2, 162.8, 162.1, 159.8, 154.4, 145.7, 131.8, 131.6, 129.8, 129.1, 129.0, 122.8, 122.8, 118.2, 116.7, 116.3, 116.0, 112.7, 61.5, 14.2. LRMS (ESI) m/z 327.1 [M+H]$^+$ and 349.1 [M+Na]$^+$. HRMS (ESI) m/z calculated for C$_{18}$H$_{16}$FN$_2$O$_3^+$ [M+H]$^+$: 327.1139; found: 327.1133.

(2) Ethyl 5-(2-aminophenyl)-2-phenyloxazole-4-carboxylate (24a)

$R_f$=0.40 (hexane/Et$_2$O=1:2, v/v). $^1$H NMR (300 MHz, CDCl$_3$) δ ppm 8.22-8.11 (m, 1H), 8.15 (d, J=7.8 Hz, 1H), 7.54-7.41 (m, 4H), 7.31 (td, J=8.7 and 1.5 Hz, 1H), 6.87 (t, J=7.5 Hz, 1H), 6.84 (d, J=8.1 Hz, 1H), 4.42 (q, J=7.2 Hz, 2H), 4.25 (bs, 2H), 1.38 (t, J=7.2 Hz, 3H). LRMS (ESI) m/z 309.3 [M+H]⁺, 331.2 [M+Na]⁺, and 347.0 [M+K]⁺. HRMS (ESI) m/z calculated for $C_{18}H_{16}N_2O_3Na^+$ [M+Na]⁺: 331.1053; found: 331.1051.

(3) Ethyl 5-(2-aminophenyl)-2-(4-chlorophenyl) oxazole-4-carboxylate (24c)

$R_f$=0.23 (hexane/Et$_2$O=1:1, v/v). ¹H NMR (300 MHz, CDCl$_3$) δ ppm 8.20 (d, J=8.1 Hz, 1H), 8.14 (dd, J=5.4 and 8.9 Hz, 2H), 7.83-7.65 (m, 3H), 7.19 (t, J=8.7 Hz, 2H), 4.44 (q, J=7.2 Hz, 2H), 1.29 (t, J=7.2 Hz, 3H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 343.1 [M+H]⁺, 365.1 [M+Na]⁺. HRMS (ESI) m/z calculated for $C_{18}H_{15}ClN_2O_3Na^+$ [M+Na]⁺: 365.0663; found: 365.0678

(4) Ethyl 5-(2-aminophenyl)-2-(4-(trifluoromethyl) phenyl)oxazole-4-carboxylate (24d)

$R_f$=0.29 (CH$_2$Cl$_2$-MeOH=20:1, v/v). ¹H NMR (300 MHz, CDCl$_3$) δ ppm 8.25 (d, J=8.1 Hz, 2H), 7.74 (d, J=8.1 Hz, 2H), 7.44 (t, J=7.8 Hz, 1H), 7.31 (t, J=7.8 Hz, 1H), 6.86 (t, J=7.5 Hz, 1H), 6.83 (d, J=7.8 Hz, 1H), 4.40 (q, J=7.2 Hz, 2H), 4.17 (s, 2H), 1.29 (t, J=7.2 Hz, 3H); ¹³C NMR (75 MHz, CDCl$_3$) δ ppm 162.0, 159.2, 155.1, 132.0, 131.6, 127.1, 126.0, 125.9, 118.2, 116.9, 112.4, 61.7, 14.2. LRMS (ESI) m/z 356.8 [M+H]⁺ and 398.9 [M+Na]⁺. HRMS (ESI) m/z calculated for $C_{18}H_{16}F_3N_2O_3^+$ [M+Na]⁺: 377.1108; found: 377.1094.

(5) Ethyl 5-(2-aminophenyl)-2-(4-methoxyphenyl) oxazole-4-carboxylate (24e)

$R_f$=0.28 (CH$_2$Cl$_2$-MeOH=20:1, v/v). ¹H NMR (300 MHz, CDCl$_3$) δ ppm 8.07 (d, J=8.7 Hz, 2H), 7.44 (d, J=7.5 Hz, 1H), 7.28 (t, J=8.1 Hz, 2H), 6.98 (d, J=8.7 Hz, 1H), 6.85 (t, J=7.5 Hz, 1H), 6.81 (d, J=7.8 Hz, 1H), 4.39 (q, J=7.2 Hz, 2H), 4.18 (bs, 2H), 1.34 (t, J=7.2 Hz, 3H); ¹³C NMR (75 MHz, CDCl$_3$) δ ppm 162.8, 162.3, 157.8, 151.9, 138.4, 130.2, 129.3, 122.7, 121.6, 119.1, 115.4, 114.4, 111.6, 61.4, 55.4, 14.2. LRMS (ESI) m/z 339.1 [M+H]⁺ and 361.1 [M+Na]⁺. HRMS (ESI) m/z calculated for $C_{19}H_{19}N_2O_4$+ [M+H]⁺: 339.1339; found: 339.1452.

(e) Synthesis of Quinolinone Derivatives Through Cyclization

(1) 2-(4-fluorophenyl)oxazolo[4,5-c]quinolin-4(5H)-one (25b)

A mixture of 24b (95 mg, 0.27 mmol), DME (7 mL) and a 2 M potassium carbonate solution (0.5 mL, 1.0 mmol) was heated to reflux for 12 h. Thereafter, the solid was collected by filtration, washed with cold EtOH, and dried under vacuum to afford 25b (45 mg, 60%).

$R_f$=0.18 (CH$_2$Cl$_2$-MeOH=1:1, v/v). ¹H NMR (300 MHz, DMSO-d$_6$) δ ppm 11.19 (bs, 1H), 7.40 (d, J=9.0 Hz, 1H), 7.38 (d, J=9.0 Hz, 1H), 7.14 (d, J=7.8 Hz, 1H), 6.71 (t, J=7.2 Hz, 1H), 6.35 (d, J=7.2 Hz, 1H), 6.59 (d, J=8.7 Hz, 1H), 6.47 (t, J=7.8 Hz, 1H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 302.7 [M+Na]⁺ and 318.8 [M+K]⁺. HRMS (ESI) m/z calculated for $C_{16}H_{10}FN_2O_2^+$ [M+H]⁺: 281.0721; found: 281.0713.

(2) 2-Phenyloxazolo[4,5-c]quinolin-4(5H)-one (25a)

$R_f$=0.30 (CH$_2$Cl$_2$-MeOH=20:1, v/v). ¹H NMR (300 MHz, DMSO-d$_6$) δ ppm 12.08 (bs, 1H), 8.29-8.18 (m, 2H), 8.05 (d, J=7.8 Hz, 1H), 7.72-7.56 (m, 4H), 7.52 (d, J=8.1 Hz, 1H), 7.37 (t, J=7.8 Hz, 1H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 262.8 [M+H]⁺, 285.2 [M+Na]⁺, and 300.6 [M+K]⁺. HRMS (ESI) m/z calculated for $C_{16}H_{11}N_2O_2^+$[M+H]⁺: 263.0815; found: 263.0845.

(3) 2-(4-Chlorophenyl)oxazolo[4,5-c]quinolin-4(5H)-one (25c)

$R_f$=0.32 (CH$_2$Cl$_2$-MeOH=20:1, v/v). ¹H NMR (300 MHz, DMSO-d$_6$) δ ppm 8.24 (d, J=8.4 Hz, 2H), 8.01 (d, J=7.5 Hz, 1H), 7.02 (t, J=8.7 Hz, 2H), 7.56 (d, J=7.5 Hz, 1H), 7.51 (t, J=8.4 Hz, 1H), 7.31 (t, J=7.5 Hz, 1H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 335.2 [M+K]⁺. HRMS (ESI) m/z calculated for $C_{16}H_9ClN_2O_2Na^+$ [M+Na]⁺: 319.0245; found: 319.0276.

(4) 2-(4-(Trifluoromethyl)phenyl)oxazolo[4,5-c] quinolin-4(5H)-one (25d)

$R_f$=0.38 (CH$_2$Cl$_2$-MeOH=20:1, v/v). ¹H NMR (300 MHz, DMSO-d$_6$) δ ppm 8.44 (d, J=8.1 Hz, 2H), 8.08 (d, J=7.8 Hz, 1H), 8.03 (d, J=8.4 Hz, 2H), 7.63 (t, J=7.2 Hz, 1H), 7.53 (d, J=8.1 Hz, 1H), 7.38 (t, J=7.5 Hz, 1H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 353.5 [M+Na]⁺ and 369.0 [M+K]⁺. HRMS (ESI) m/z calculated for $C_{17}H_{10}F_3N_2O_2^+$ [M+H]⁺: 331.0689; found: 331.0682.

(5) 2-(4-Methoxyphenyl)oxazolo[4,5-c]quinolin-4(5H)-one (25e)

$R_f$=0.28 (CH$_2$Cl$_2$-MeOH=20:1, v/v). ¹H NMR (300 MHz, DMSO-d$_6$) δ ppm 11.18 (bs, 1H), 7.38-7.31 (m, 1H), 7.33 (d, J=9.0 Hz, 1H), 7.19 (dd, J=1.2 and 8.1 Hz, 1H), 6.76 (td, J=8.4 and 1.5 Hz, 1H), 6.68 (d, J=9.0 Hz, 1H), 6.53 (td, J=8.1 and 1.2 Hz, 1H), 6.41-6.33 (m, 1H), 6.35 (d, J=9.0 Hz, 1H); ¹³C NMR (75 MHz, CDCl$_3$) δ ppm 166.3, 161.3, 160.6, 151.0, 148.5, 132.9, 132.6, 131.3, 130.2, 129.3, 129.2, 124.9, 122.6, 122.5, 122.5, 116.3, 116.0, 61.6, 14.0. LRMS (ESI) m/z 293.1 [M+H]⁺, 314.9 [M+Na]⁺, and 331.0 [M+K]⁺. HRMS (ESI) m/z calculated for $C_{17}H_{13}N_2O_3$+[M+H]⁺: 293.0921; found: 293.0919.

(f) Synthesis of Quinolinone Derivatives as Final Compounds Through Alkylation

(1) 5-(2-(dimethylamino)ethyl)-2-(4-fluorophenyl) oxazolo[4,5-c]quinolin-4(5H)-one (3)

DMF (5 mL) was added to 25b (43 mg, 0.153 mmol), 2-bromo-N,N-dimethylethanaminehydrobromide (80 mg, 0.31 mmol, 1.2 eq.), and potassium carbonate (63 mg, 0.46 mmol, 3.0 eq.). The mixture was stirred at 130° C. for 3 h. After cooling to room temperature, the reaction mixture was evaporated under vacuum to remove the solvent and purified by silica gel column chromatography using Et$_2$O-MeOH (10:1 to 3:1, v/v) as the eluent, giving the compound of Formula 3.

Yield: 39%. R$_f$=0.15 (EtO$_2$-MeOH=5:1, v/v). $^1$H NMR (300 MHz, CDCl$_3$) δ ppm 8.33-8.22 (m, 1H), 8.29 (dd, J=5.4 and 8.7 Hz, 1H), 8.03 (dd, J=1.5 and 8.0 Hz, 1H), 7.64 (td, J=7.2 and 1.2 Hz, 1H), 7.57 (d, J=8.4 Hz, 1H), 7.38 (t, J=6.9 Hz, 1H), 7.22 (t, J=8.4 Hz, 1H), 7.27-7.16 (m, 1H), 4.58 (t, J=7.8 Hz, 2H), 2.66 (t, J=7.8 Hz, 2H), 2.41 (s, 6H); $^{13}$C NMR (75 MHz, CDCl$_3$) δ ppm 166.5, 163.1, 161.7, 157.3, 152.3, 130.5, 129.8, 129.7, 129.6, 122.8, 122.8, 121.9, 116.4, 116.1, 115.4, 111.6, 56.3, 45.9, 40.8, 29.7, 22.7. LRMS (ESI) m/z 352.2 [M+H]$^+$ and 374.0 [M+Na]$^+$. HRMS (ESI) m/z calculated for C$_{18}$H$_{19}$FN$_3$O$_2$+[M+H]$^+$: 352.1456; found: 352.1496.

(2) 5-(2-(dimethylamino)ethyl)-2-phenyloxazolo[4,5-c]quinolin-4(5H)-one (2)

Yield: 39%. R$_f$=0.25 (Et$_2$O-MeOH=5:1, v/v). $^1$H NMR (300 MHz, CDCl$_3$) δ ppm 8.34-8.27 (m, 2H), 8.07 (dd, J=1.5 and 7.8 Hz, 1H), 7.69-7.51 (m, 5H), 7.38 (td, J=7.2 and 1.2 Hz, 1H), 4.59 (t, J=7.5 Hz, 2H), 2.68 (t, J=7.5 Hz, 2H), 2.41 (s, 6H); $^{13}$C NMR (75 MHz, CDCl$_3$) δ ppm 162.6, 157.4, 152.3, 137.9, 131.6, 130.5, 130.0, 129.0, 127.4, 126.5, 122.6, 122.0, 115.4, 111.8, 56.3, 45.9, 40.9. LRMS (ESI) m/z 333.4 [M+H]$^+$ and 355.3 [M+Na]$^+$. HRMS (ESI) m/z calculated for C$_{20}$H$_{20}$N$_3$O$_2$$^+$ [M+H]$^+$: 334.1550; found: 334.1557.

(3) 2-(4-chlorophenyl)-5-(2-(dimethylamino)ethyl)oxazolo[4,5-c]quinolin-4(5H)-one (4)

Yield: 26%. R$_f$=0.17 (Et$_2$O-MeOH=5:1, v/v). $^1$H NMR (300 MHz, CDCl$_3$) δ ppm 8.24 (d, J=8.7 Hz, 2H), 8.04 (d, J=8.1 Hz, 1H), 7.96 (d, J=8.4 Hz, 1H), 7.68 (td, J=7.5 and 1.5 Hz, 1H), 7.53 (d, J=8.7 Hz, 2H), 7.42 (t, J=7.8 Hz, 1H), 4.43 (t, J=5.1 Hz, 2H), 2.86 (t, J=5.1 Hz, 2H), 2.41 (s, 6H); $^{13}$C NMR (75 MHz, CDCl$_3$) δ ppm 151.6, 138.1, 136.9, 130.6, 129.4, 129.0, 128.7, 127.5, 123.5, 121.44, 113.7, 109.5, 57.3, 53.4, 45.8, 29.7. LRMS (ESI) m/z 368.0 [M+H]$^+$ and 390.2 [M+Na]$^+$. HRMS (ESI) m/z calculated for C$_{20}$H$_{19}$ClN$_3$O$_2$$^+$ [M+H]$^+$: 368.1160; found: 368.1202.

(4) 5-(2-(dimethylamino)ethyl)-2-(4-(trifluoromethyl)phenyl)oxazolo[4,5-c]quinolin-4(5H)-one (5)

Yield: 37%. R$_f$=0.13 (Et$_2$O-MeOH=5:1, v/v). $^1$H NMR (300 MHz, CDCl$_3$) δ ppm 8.43 (d, J=8.1 Hz, 2H), 8.09 (dd, J=1.2 and 7.8 Hz, 1H), 7.81 (d, J=8.4 Hz, 2H), 7.68 (dddd, J=1.5, 7.2, and 8.7 Hz, 1H), 7.60 (d, J=8.4 Hz, 1H), 7.41 (td, J=7.8 and 0.9 Hz, 1H), 4.60 (t, J=7.5 Hz, 2H), 2.68 (t, J=7.8 Hz, 2H), 2.42 (s, 6H); $^{13}$C NMR (75 MHz, CDCl$_3$) δ ppm 161.0, 157.3, 152.8, 138.1, 131.0, 127.7, 126.1, 126.1, 126.0, 126.0, 122.8, 122.1, 115.5, 111.5, 56.3, 45.9, 37.6. LRMS (ESI) m/z 402.1 [M+H]$^+$ and 424.1 [M+Na]$^+$. HRMS (ESI) m/z calculated for C$_{21}$H$_{19}$F$_3$N$_3$O$_2$+[M+H]$^+$: 402.1424; found: 402.1426.

(5) 5-(2-(dimethylamino)ethyl)-2-(4-methoxyphenyl)oxazolo[4,5-c]quinolin-4(5H)-one (6)

Yield: 18%. R$_f$=0.08 (Et$_2$O-MeOH=5:1, v/v). $^1$H NMR (300 MHz, CDCl$_3$) δ ppm 8.24 (d, J=9.0 Hz, 2H), 8.04 (d, J=8.4 Hz, 1H), 7.64-7.60 (m, 2H), 7.40-7.33 (m, 1H), 7.04 (d, J=8.7 Hz, 2H), 4.62 (t, J=7.5 Hz, 2H), 3.09 (s, 3H), 2.72 (t, J=7.8 Hz, 2H), 2.44 (s, 6H); $^{13}$C NMR (75 MHz, CDCl$_3$) δ ppm 162.8, 162.4, 157.5, 152.0, 137.6, 130.1, 129.9, 129.4, 122.6, 121.8, 119.1, 115.4, 114.4, 111.8, 56.0, 55.5, 45.6, 40.5, 29.7. LRMS (ESI) m/z 364.1 [M+H]$^+$ and 387.1 [M+Na]$^+$. HRMS (ESI) m/z calculated for C$_{21}$H$_{22}$N$_3$O$_3$$^+$ [M+H]$^+$: 364.1656; found: 364.1694.

(6) N,N-dimethyl-2-((2-phenyloxazolo[4,5-c]quinolin-4-yl)oxy)ethanamine (7)

Yield: 9%. R$_f$=0.36 (Et$_2$O-MeOH=5:1, v/v). $^1$H NMR (300 MHz, CDCl$_3$) δ ppm 8.38-8.31 (m, 2H), 8.16 (dd, J=0.9 and 8.1 Hz, 1H), 7.96 (d, J=8.4 Hz, 1H), 7.66 (td, J=7.2 and 1.5 Hz, 1H), 7.59-7.48 (m, 4H), 4.84 (t, J=6.0 Hz, 2H), 2.94 (t, J=6.0 Hz, 1H), 2.42 (s, 6H); $^{13}$C NMR (75 MHz, CDCl$_3$) δ ppm 163.0, 154.7, 153.9, 144.2, 131.6, 129.1, 129.0, 127.9, 127.6, 126.7, 126.5, 124.7, 120.3, 114.7, 64.1, 57.9, 45.9. LRMS (ESI) m/z 333.9 [M+H]$^+$ and 356.9 [M+Na]$^+$. HRMS (ESI) m/z calculated for C$_{20}$H$_{20}$N$_3$O$_2$+[M+H]$^+$: 334.1550; found: 334.1552.

(7) 2-((2-(4-fluorophenyl)oxazolo[4,5-c]quinolin-4-yl)oxy)-N,N-dimethylethanamine (8)

Yield: 9%. R$_f$=0.30 (Et$_2$O-MeOH=5:1, v/v). $^1$H NMR (300 MHz, CDCl$_3$) δ ppm 8.41-8.28 (m, 11H), 8.29 (dd, J=5.4 and 9.0 Hz, 1H), 8.14 (d, J=8.1 Hz, 1H), 7.96 (d, J=8.1 Hz, 1H), 7.67 (ddd, J=1.5, 7.1, and 8.4 Hz, 1H), 7.52 (td, J=8.0 and 0.9 Hz, 1H), 7.29-7.18 (m, 2H), 4.83 (t, J=6.0 Hz, 2H), 2.93 (t, J=6.0 Hz, 2H), 2.41 (s, 6H); $^{13}$C NMR (75 MHz, CDCl$_3$) δ ppm 166.6, 163.2, 161.8, 154.6, 153.9, 144.2, 129.9, 129.8, 128.0, 126.4, 124.8, 123.0, 123.0, 120.2, 116.4, 116.1, 114.6, 64.1, 57.9, 45.8, 29.7.
LRMS (ESI) m/z 352.2 [M+H]$^+$ and 374.0 [M+Na]$^+$. HRMS (ESI) m/z calculated for C$_{20}$H$_{19}$FN$_3$O$_2$$^+$ [M+H]$^+$: 352.1456; found: 352.1498.

(8) 2-((2-(4-chlorophenyl)oxazolo[4,5-c]quinolin-4-yl)oxy)-N,N-dimethylethanamine (9)

Yield: 8%. R$_f$=0.28 (Et$_2$O-MeOH=5:1, v/v). $^1$H NMR (300 MHz, CDCl$_3$) δ ppm 8.27 (d, J=8.4 Hz, 2H), 8.14 (d, J=8.1 Hz, 1H), 7.96 (d, J=8.1 Hz, 1H), 7.67 (t, J=7.5 Hz, 1H), 7.53 (d, J=8.1 Hz, 3H), 4.84 (t, J=5.1 Hz, 2H), 2.94 (t, J=5.1 Hz, 2H), 2.42 (s, 6H); $^{13}$C NMR (75 MHz, CDCl$_3$) δ ppm 161.7, 154.6, 153.9, 144.3, 138.0, 129.4, 129.3, 128.4, 128.0, 126.4, 125.2, 124.8, 120.2, 114.6, 64.8, 57.9, 53.4, 45.8, 31.9. LRMS (ESI) m/z 368.2 [M+H]$^+$ and 390.2 [M+Na]$^+$. HRMS (ESI) m/z calculated for C$_{20}$H$_{19}$ClN$_3$O$_2$$^+$ [M+H]$^+$: 368.1160; found: 368.1195.

(9) N,N-dimethyl-2-((2-(4-(trifluoromethyl)phenyl)oxazolo[4,5-c]quinolin-4-yl)oxy)ethanamine (10)

Yield: 10%. R$_f$=0.38 (Et$_2$O-MeOH=5:1, v/v). $^1$H NMR (300 MHz, CDCl$_3$) δ ppm 8.47 (d, J=8.1 Hz, 2H), 8.18 (d, J=7.8 Hz, 1H), 7.98 (d, J=8.4 Hz, 1H), 7.82 (d, J=8.4 Hz, 2H), 7.69 (td, J=7.2 and 1.5 Hz, 1H), 7.54 (td, J=7.2 and 1.2 Hz, 1H), 4.49 (t, J=6.3 Hz, 2H), 2.94 (t, J=6.0 Hz, 2H), 2.42 (s, 6H); $^{13}$C NMR (75 MHz, CDCl$_3$) δ ppm 166.1, 154.7, 154.1, 144.4, 129.8, 129.5, 128.0, 127.8, 126.4, 126.0, 126.0, 124.9, 120.4, 114.5, 64.2, 59.6, 45.9. LRMS (ESI) m/z 402.1 [M+H]$^+$ and 424.1 [M+Na]$^+$. HRMS (ESI) m/z calculated for C$_{21}$H$_{19}$F$_3$N$_3$O$_2$+[M+H]$^+$: 402.1424; found: 402.1437.

(10) 2-((2-(4-methoxyphenyl)oxazolo[4,5-c]quinolin-4-yl)oxy)-N,N-dimethylethanamine (11)

Yield: 15%. R$_f$=0.18 (Et$_2$O-MeOH=5:1, v/v). $^1$H NMR (300 MHz, CDCl$_3$) δ ppm 8.26 (d, J=8.1 Hz, 2H), 8.16 (d, J=6.3 Hz, 1H), 7.96 (d, J=8.4 Hz, 1H), 7.66 (dd, J=6.9 and 14.3 Hz, 1H), 7.54 (dd, J=7.8 and 16.2 Hz, 1H), 7.05 (d, J=8.7 Hz, 2H), 4.86 (t, J=6.3 Hz, 2H), 3.91 (s, 3H), 3.01 (t, J=6.3 Hz, 2H), 2.47 (s, 6H); $^{13}C$ NMR (75 MHz, CDCl$_3$) δ ppm 163.0, 162.5, 154.6, 153.6, 144.0, 129.4, 128.8, 127.9, 126.5, 124.7, 120.2, 119.2, 114.8, 114.5, 63.7, 57.8, 55.5, 45.6, 30.4. LRMS (ESI) m/z 364.5 [M+H]$^+$ and 387.5 [M+Na]$^+$. HRMS (ESI) m/z calculated for $C_{21}H_{22}N_3O_3^+$ [M+H]$^+$: 364.1656; found: 364.1693.

(11) 5-(2-(diethylamino)ethyl)-2-(4-fluorophenyl) oxazolo[4,5-c]quinolin-4(5H)-one (12)

Yield: 14%. $R_f$=0.39 (Et$_2$O-MeOH=5:1, v/v). $^1H$ NMR (300 MHz, CDCl$_3$) δ ppm 8.35-8.26 (m, 1H), 8.30 (dd, J=5.4 and 8.7 Hz, 1H), 8.03 (d, J=7.5 Hz, 1H), 7.66-7.59 (m, 2H), 7.43-7.34 (m, 1H), 7.22 (t, J=8.7 Hz, 2H), 4.55 (t, J=7.8 Hz, 2H), 2.79 (t, J=7.8 Hz, 2H), 2.68 (dd, J=7.2 and 14.4 Hz, 4H), 1.09 (t, J=7.2 Hz, 6H); $^{13}C$ NMR (75 MHz, CDCl$_3$) δ ppm 166.5, 163.2, 161.7, 157.4, 152.3, 138.0, 130.5, 129.8, 129.7, 129.6, 122.8, 122.8, 122.6, 121.8, 116.4, 116.1, 115.6, 111.6, 50.0, 47.6, 41.2, 12.0. LRMS (ESI) m/z 380.3 [M+H]$^+$. HRMS (ESI) m/z calculated for $C22H_{23}FN_3O_2^+$ [M+H]$^+$: 380.1769; found: 380.1817.

(12) N,N-diethyl-2-((2-(4-fluorophenyl)oxazolo[4,5-c]quinolin-4-yl)oxy)ethanamine (13)

Yield: 8%. $R_f$=0.51 (Et$_2$O-MeOH=5:1, v/v). $^1H$ NMR (300 MHz, CDCl$_3$) δ ppm 8.38-8.31 (m, 1H), 8.35 (dd, J=5.4 and 9.0 Hz, 1H), 8.14 (d, J=7.8 Hz, 1H), 7.96 (d, J=8.4 Hz, 1H), 7.66 (ddd, J=1.5, 7.1, and 8.4 Hz, 1H), 7.52 (t, J=7.5 Hz, 1H), 7.28-7.19 (m, 2H), 4.81 (t, J=6.9 Hz, 2H), 3.06 (t, J=6.9 Hz, 2H), 2.72 (dd, J=7.2 and 14.4 Hz, 4H), 1.14 (t, J=7.2 Hz, 6H); $^{13}C$ NMR (75 MHz, CDCl$_3$) δ ppm 166.6, 163.2, 161.8, 154.6, 153.8, 144.2, 129.9, 129.8, 129.1, 128.0, 126.4, 124.7, 123.0, 123.0, 120.2, 116.5, 116.2, 114.6, 64.2, 51.0, 47.7, 29.7, 11.8. LRMS (ESI) m/z 380.3 [M+H]$^+$. HRMS (ESI) m/z calculated for $C_{22}H_{23}FN_3O_2^+$ [M+H]$^+$: 380.1769; found: 380.1814.

(13) 5-(2-(diethylamino)ethyl)-2-(4-(trifluoromethyl)phenyl)oxazolo[4,5-c]quinolin-4(5H)-one (14)

Yield: 27%. $R_f$=0.39 (Et$_2$O-MeOH=5:1, v/v). $^1H$ NMR (300 MHz, CDCl$_3$) δ ppm 8.44 (d, J=8.1 Hz, 2H), 8.08 (d, J=7.8 Hz, 1H), 7.81 (d, J=8.1 Hz, 2H), 7.71-7.60 (m, 2H), 7.70 (t, J=7.8 Hz, 1H), 4.56 (t, J=7.8 Hz, 2H), 2.80 (t, J=8.1 Hz, 2H), 2.69 (dd, J=7.2 and 14.4 Hz, 4H), 1.09 (t, J=7.2 Hz, 6H).

(14) N,N-diethyl-2-((2-(4-(trifluoromethyl)phenyl) oxazolo[4,5-c]quinolin-4-yl)oxy)ethanamine (15)

Yield: 50%. $R_f$=0.51 (Et$_2$O-MeOH=5:1, v/v). 1HNMR (300 MHz, CDCl$_3$) δ ppm 8.45 (d, J=8.1 Hz, 2H), 8.15 (d, J=8.7 Hz, 1H), 7.95 (d, J=8.4 Hz, 1H), 7.80 (d, J=8.4 Hz, 2H), 7.68 (ddd, J=1.5, 7.1, and 8.4 Hz, 1H), 7.53 (t, J=7.2 Hz, 1H), 4.81 (t, J=6.9 Hz, 2H), 3.06 (t, J=7.2 Hz, 2H), 2.72 (dd, J=7.2 and 14.4 Hz, 4H), 1.09 (t, J=7.2 Hz, 6H).

Experimental Example 1: Evaluation of Inhibitory Efficacy on TSLP-TSLPR Interaction by ELISA In this example, an investigation was made as to whether the inventive quinolinone derivative compounds directly inhibit the binding of TSLP to TSLP receptor. To this end, home-made FLAG-TSLP protein and TSLPR-His protein were used to establish an ELISA-based TSLP-TSLPR interaction assay for measuring reactions with HRP. The inhibitory activities of the inventive compounds were evaluated by the interaction assay.

ELISA assay was conducted using an Ni-NTA HisSorb plate (Qiagen, Germany). 100 μL of a solution of TSLPR C-terminally tagged with hexahistidine (His) was dispensed into each well of the plate and incubated at room temperature for 2 h. After each well was washed twice with 200 μL of PBS and 0.05% Tween-20, 100 μL of a solution of each of the inventive compounds as a sample and 100 μL of TSLP N-terminally tagged with FLAG was dispensed into the well. After incubation at 4° C. overnight, each well was washed twice and treated with 100 μL of a blocking buffer (PBS-0.05% Tween 20 and 1% nonfat dry milk). The plate was washed twice, coated with 100 μL of a monoclonal anti-FLAG horseradish peroxidase antibody (Sigma-Aldrich Co., USA) for 2 h, and incubated at room temperature. Then, each well was washed 5 times, treated with 200 μL of a solution of o-phenylenediaminedihydrochloride (Sigma-Aldrich Co., USA), incubated for 30 min, and added with 1 N HCl.

Optical densities (ODs) were measured at 450 nm using a microplate spectrophotometer. The inhibitory effect of the compound on TSLP-TSLPR interaction was calculated using the following equation:

Inhibition (inhibitory effect) (%)=(1−OD$_{sample}$/OD$_{control}$)×100

The results are shown in Table 1.

TABLE 1

| Compound | Inhibition (%) | | |
|---|---|---|---|
| | 0.1 mM | 0.3 mM | 1 mM |
| 2 | 26.7 | 49.0 | 66.9 |
| 3 | 17.7 | 27.5 | N/D |
| 4 | 28.8 | 46.6 | N/D |
| 5 | 23.2 | 29.6 | N/D |
| 6 | 25.8 | 54.7 | N/D |
| 7 | 27.8 | 54.6 | 57.2 |
| FLAG tag-free TSLP (1 mg/mL) | | 40.7 | |

N/D: Not determined

Experimental Example 2: Evaluation of Inhibitory Efficacy on IL-6 Secretion by IL-33 Inhibition First, HMC-1, a human mast cell line, was cultured until an appropriate number of cells was maintained in a 96-well plate. Mixtures of IL-33 and different concentrations (0.3, 3, and 30 μM) of each of the inventive compounds were treated on cells, incubated at 37° C. for 24 h, and centrifuged. The supernatants were analyzed for IL-6 secretion using an IL-6 ELISA kit (Biolegend, USA). The results are shown in Table 2.

TABLE 2

| Compound | Inhibition of IL-6 secretion (%) | | |
|---|---|---|---|
| | 0.03 μM | 0.3 μM | 3 μM |
| 2 | — | | −11.8 |
| 3 | — | | 29.8 |
| 4 | | 22.5 | 29.7 |

TABLE 2-continued

| | Inhibition of IL-6 secretion (%) | | |
|---|---|---|---|
| Compound | 0.03 μM | 0.3 μM | 3 μM |
| 5 | | 30.4 | 28.2 |
| 6 | | — | −57.8 |
| 7 | | — | 35.6 |
| 10 | 32.7 | 49.3 | 51.3 |
| 11 | | — | −216.4 |
| IL-33 only | | 0 | |

Negative (−) values indicate increased IL-6 secretion

Taken together, these results demonstrate that the inventive quinolinone derivatives effectively inhibit TSLP and IL-33, key cytokines inducing allergic diseases such as asthma or atopic dermatitis, from binding to their receptors. In conclusion, the inventive quinolinone derivatives can be used to fundamentally prevent and treat allergic diseases such as asthma or atopic dermatitis due to their ability to inhibit TSLP- or IL-33-mediated signal transduction.

Figure 8:
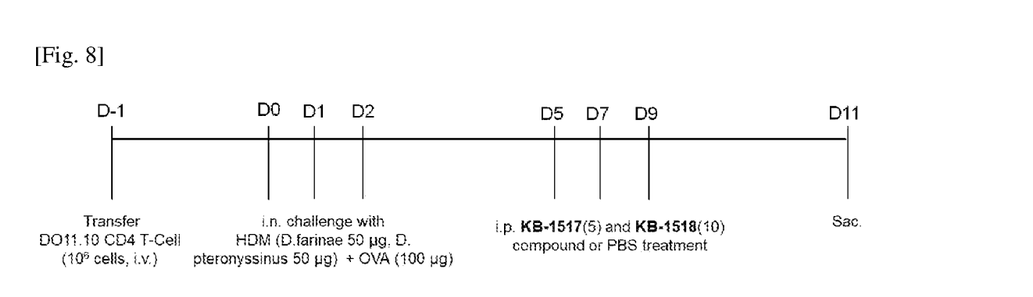
FIG. 8 shows the treatment schedule with the Formula 5 (KB 1517) and Formula 10 (KB 1518) (200 μg each) according to the present invention in house dust mite (HDM)-induced allergic airway inflammation mouse models.

Experimental Example 3: House Dust Mite (HDM)-Induced Allergic Airway Inflammation Mouse Models Splenocytes were isolated from DO11.10 mice and ~1×10⁶CD4T cells were transferred to pure BALB/c mice by intravenous injection. For 3 days from the next day, 100 μg of a mixture of HDM (Dermatophagoidesfarinae 50 μg, Dermatophagoidespteronyssinus 50 μg, Greer Laboratories, Inc., USA) and OVA (Sigma-Aldrich Co., USA) was administered intranasally to the mice. From day 2 after administration, the mice were treated with 200 μg of each of the inventive compounds or PBS (for control mice) three times daily through the intraperitoneal route. After the mice were euthanized on day 11, the numbers of total cells and eosinophils in the airways were checked. The treatment schedule with the Formula 5 (KB 1517) and Formula 10 (KB 1518) (200 μg each) in house dust mite (HDM)-induced allergic airway inflammation mouse models is shown in FIG. 8. The results are shown in FIGS. 4 and 5.

Figure 1:
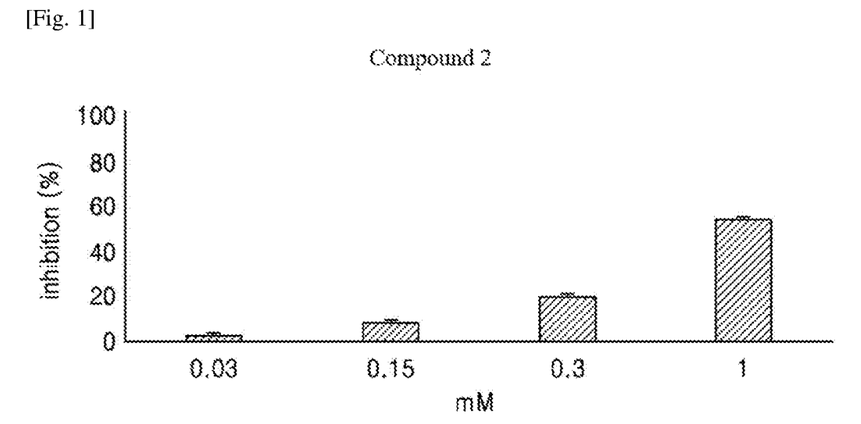
FIG. 1 is a histogram showing the inhibitory effect of the compound of Formula 2 according to the present invention on TSLP-TSLPR interaction, which was evaluated by ELISA.
Figure 2:
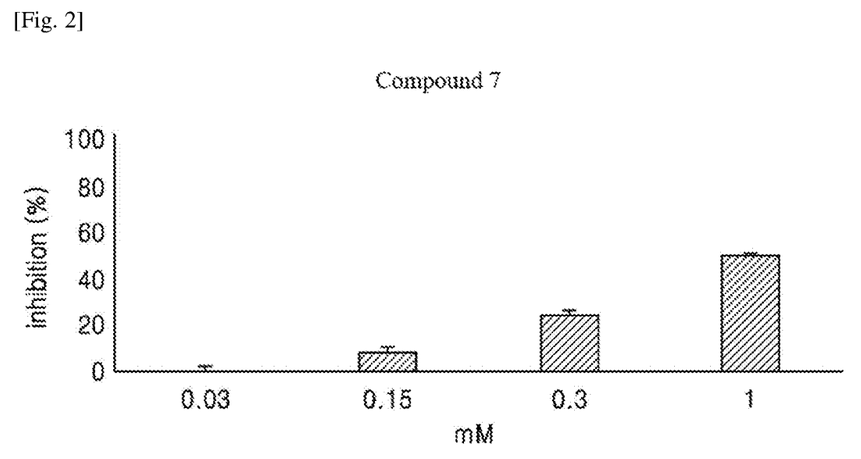
FIG. 2 is a histogram showing the inhibitory effect of the compound of Formula 7 according to the present invention on TSLP-TSLPR interaction, which was evaluated by ELISA.
Figure 3:
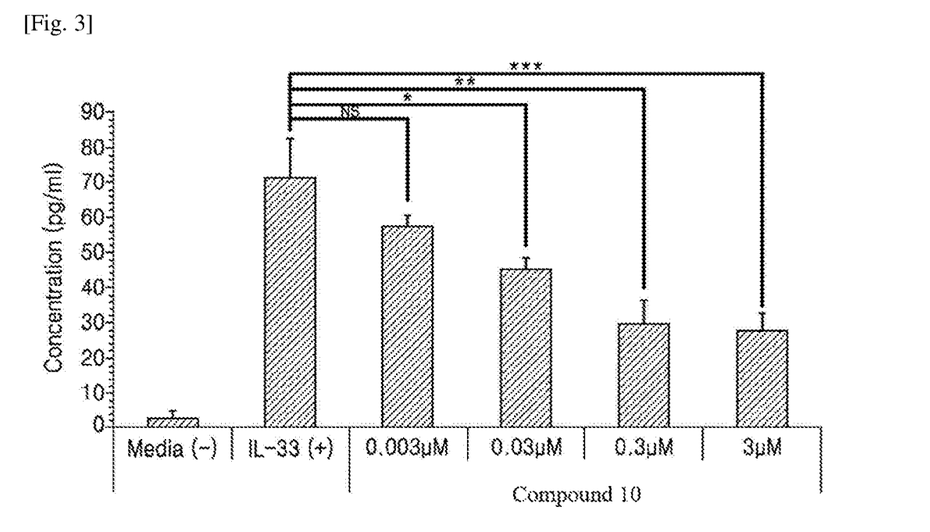
FIG. 3 is a histogram showing the inhibitory effect of the compound of Formula 10 according to the present invention on IL-6 secretion by IL-33 inhibition.
Figure 4:
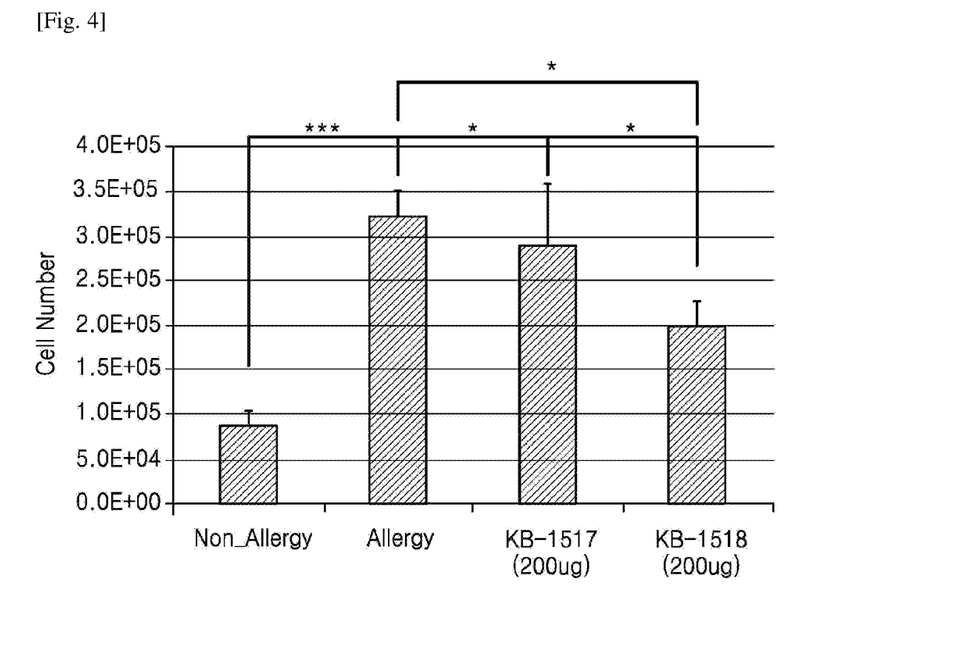
FIGS. 4 and 5 show the numbers of total cells and eosinophils in the airways of house dust mite (HDM)-induced allergic airway inflammation mouse models treated with the compounds of Formula 5 (KB-1517) and Formula 10 (KB-1518) (200 μg each) according to the present invention to investigate the effects of the compounds.
Figure 5:
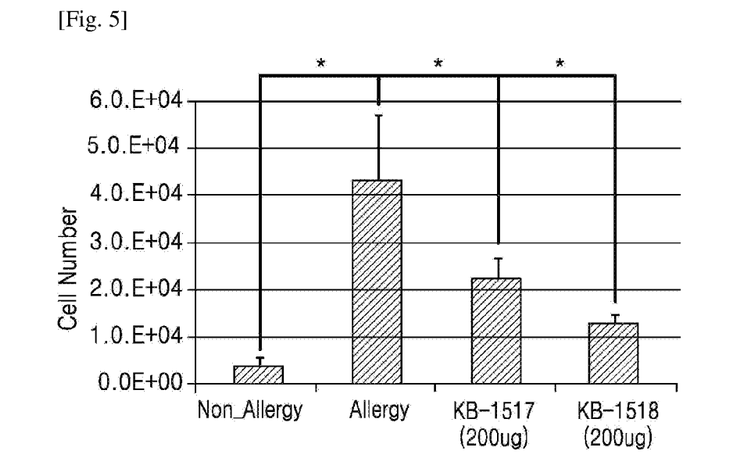
Figure 6:
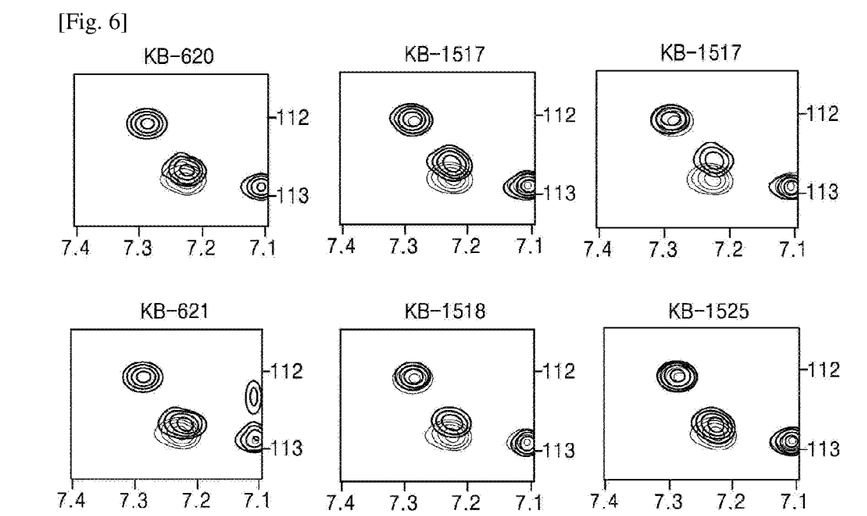
FIG. 6 shows the chemical shift perturbations of Thr 120 of IL-33 protein by compounds of the present invention.
Figure 7:
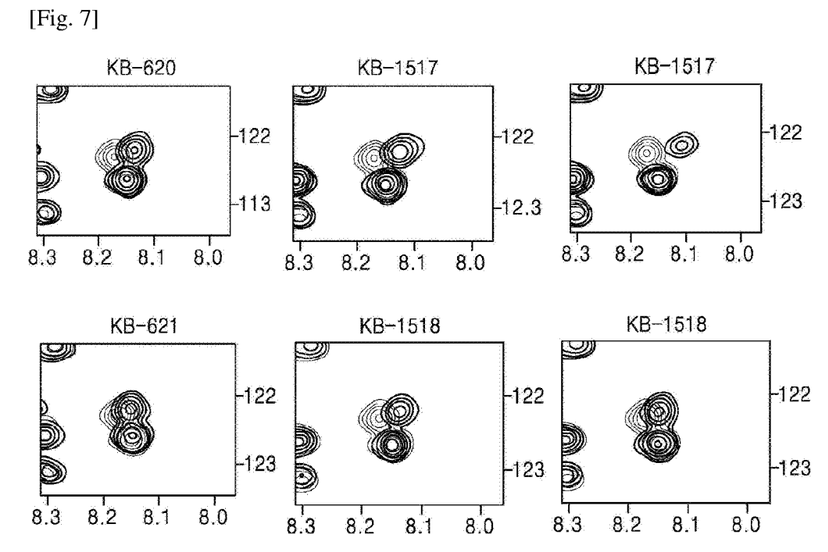
FIG. 7 shows the chemical shift perturbations of Glu 121 of IL-33 protein by compounds of the present invention.

As can be seen from FIGS. 4 and 5, the numbers of total cells and eosinophils in the airways of the mice treated with the inventive compounds of Formula 5 (KB-1517) and Formula 10 (KB-1518) (200 μg each) were significantly reduced than those in the untreated controls. These results lead to the conclusion that the inventive quinolinone derivatives can be used to fundamentally prevent and treat allergic diseases such as asthma atopic dermatitis.

Experimental Example 4: 2D NMR Spectrometry

Measurements were done using a Bruker 600 MHz NMR spectrometer (triple-resonance, pulsed field gradient probe (Bruker, Germany)) at 25° C. 2D $^1$H-$^{15}$NHSQC spectra of IL-33 were measured in the same molar ratio with/without each of the compounds. The 2D data were processed and analyzed using the TopSpin 3.1 program (Bruker, Germany).

Chemical shift perturbations (CSPs) were calculated using the following equation:

$$CSP = \sqrt{(\Delta\delta_{1H})^2 + \frac{(\Delta\delta_{15N})^2}{5}}$$

where $\Delta\delta_{1H}$ and $\Delta\delta_{15N}$ indicate H and $^{15}$N chemical shift differences, respectively.

Experimental Example 5: IL-33 Protein Expression and Purification

IL-33 was cloned into an expression vector pPROEX, an N-terminal His-tag fusion protein, in *E. coli* BL21 (DE3). When the cell density (OD$_{600}$) reached 0.6, cells were induced with 0.5 mM isopropyl-1-D-thiogalactoside (IPTG) and were allowed to further grow at 20° C. overnight. To obtain uniformly labeled $^5$N IL-33, the bacterial cells were grown in M9 minimal medium containing $^{15}$N NH$_4$Cl. Cells were harvested and resuspended in lysis buffer (0.1 M Tris pH 7.4, 0.3 M NaCl, 1 mM β-mercaptoethanol, 0.1% TritonX100, and 0.1 mM phenylmethylsulfonyl fluoride). Cells were lysed by sonication in an ice bath. The cell lysate was centrifuged at 10000×g and 4° C. for 25 min. The pellets were discarded and the supernatant was eluted with 50 mM sodium phosphate (pH 7.4), 300 mM sodium chloride, and 1 mM β-mercaptoethanol from a 5 mL HisPur cobalt resin column (Thermo Scientific Inc.). Thereafter, the buffer was exchanged with 50 mM sodium phosphate (pH 7.4), 300 mM sodium chloride, 1 mM β-mercaptoethanol, and 250 mM imidazole. The fusion protein was cleaved with TEV protease in dialysis buffer (Tris 20 mM (pH 7.4), sodium chloride 300 mM) at 4° C. The IL-33-containing mixture was loaded onto a HisPur cobalt resin column and washed with 0.1 M Tris (pH 7.4), 0.3 M sodium chloride, and 1 mM β-mercaptoethanol. Thereafter, the bound protein was eluted with 0.1 M Tris (pH 7.4), 0.3 M sodium chloride and 1 mM p-mercaptoethanol (20 mL). The eluate was loaded onto a Superdex S75 gel filtration column (16/60 GE Healthcare) equilibrated with a buffer containing 20 mM sodium phosphate (pH 6.8), 100 mM sodium chloride, and 5 mM BME to obtain pure IL-33 protein.

INDUSTRIAL APPLICABILITY

The quinolinone derivative compounds of the present invention can effectively suppress inflammatory responses of an allergic disease such as asthma or atopic dermatitis. In addition, the pharmaceutical composition of the present invention can be used to fundamentally prevent or treat various allergic diseases such as asthma or atopic dermatitis.

The invention claimed is:

1. A quinolinone derivative represented by Formula 1a or Formula 1 b:

[Formula 1a]

wherein R$_1$ and R2 are identical to or different from each other and are each independently selected from C$_1$-C$_4$ alkyl groups, and —Z-alkyl (wherein Z is selected from O, S, or is —(CH$_2$)$_m$— wherein m is an integer from 0 to 5), X and Y are each independently selected from hydrogen, halogen groups, a hydroxyl group, an amino group, a nitro A group, a cyano group, a trifluoromethyl group, CO—R' (wherein R' is a $C_1$-$C_4$ alkyl group), NHR' (wherein R' is a $C_1$-$C_4$ alkyl group), NR'R' (wherein each R' is independently a $C_1$-$C_4$ alkyl group), NHCOR' (wherein R' is a $C_1$-$C_4$ alkyl group), and COOR' (wherein R' is a $C_1$-$C_4$ alkyl group), p is an integer from 0 to 4, provided that when p is an integer of 2 or more, the Y groups are identical to or different from each other, and q is an integer from 0 to 5, provided that when q is an integer of 2 or more, the X groups are identical to or different from each other,

[Formula 1b]

wherein $R_1$, $R_2$, X, Y, p, and q are as defined in Formula 1a.

2. A quinolinone derivative represented by Formula 1a or Formula 1b selected from the group consisting of the following compounds:

[Formula 2]

[Formula 3]

[Formula 4]

[Formula 5]

[Formula 6]

[Formula 7]

[Formula 8]

[Formula 9]

[Formula 10]

[Formula 11]

[Formula 12]

[Formula 13]

[Formula 14]

and

[Formula 15]

3. A pharmaceutical composition for preventing or treating an allergic disease comprising the quinolinone derivative of claim 1 as an active ingredient and a pharmaceutically acceptable carrier.

* * * * *